United States Patent [19]
Fischer

[11] 3,948,634
[45] Apr. 6, 1976

[54] HERBICIDE
[75] Inventor: Adolf Fischer, Mutterstadt, Germany
[73] Assignee: BASF Aktiengesellschaft, Ludwigshafen (Rhine), Germany
[22] Filed: May 9, 1974
[21] Appl. No.: 468,371

Related U.S. Application Data
[63] Continuation-in-part of Ser. No. 299,597, Oct. 20, 1972, abandoned.

[30] Foreign Application Priority Data
Nov. 6, 1971  Germany............................ 2155284

[52] U.S. Cl........................................ 71/91; 71/111
[51] Int. Cl.$^2$............................................ A01N 9/22
[58] Field of Search................................. 71/91, 111

[56] References Cited
UNITED STATES PATENTS
3,708,277  1/1973  Zeidler et al. ...................... 71/91 X OTHER PUBLICATIONS
Thompson, "Agricultural Chemicals — Book II – Herbicides" pp. 96, 97.

Primary Examiner—Lewis Gotts
Assistant Examiner—Catherine L. Mills
Attorney, Agent, or Firm—Johnston, Keil, Thompson & Shurtleff

[57] ABSTRACT

Herbicide compositions embodying a mixture of a 3-alkyl or cycloalkyl-2,1,3-benzothiadiazinone-(4)-2,2-dioxide or a salt thereof and methyl phenylcarbamates; and selective herbicide processes.

4 Claims, No Drawings

HERBICIDE

RELATED APPLICATION

This application is a continuation-in-part of my application Ser. No. 299,597, filed Oct. 20, 1972, now abandoned, the disclosure of which is incorporated herein by reference.

The present invention relates to herbicides containing mixtures of various active ingredients.

It is known that substituted acid anilides, carbamates, phosphoric esters and benzothiadiazinones have a herbicidal action. However, their action is not always satisfactory.

I have now found that a composition of
a. a compound of the formula $$\text{benzothiadiazinone structure with N-R, SO}_2, \text{NH}$$

where R denotes lower alkyl or cycloalkyl or their salts (alkali metal, alkaline earth metal, ammonium, hydroxyalkyl or alkylammonium), and b. a compound of the formula $$X\text{-phenyl-NH-C(=O)-OCH}_3, \text{ with Cl substituent}$$

where X denotes chlorine or bromine, has a herbicidal action superior to that of the individual active ingredients.

The composition of the invention is suitable for controlling unwanted plants in crops, e.g., rice and Indian corn.

The compositions according to the invention may be used as solutions, emulsions, suspensions, dusts or in granular form. The form of application depends entirely on the purpose for which the agents are being used; in any case it should ensure a fine distribution of the active ingredient.

For the preparation of solution to be sprayed direct, mineral oil fractions of medium to high boiling point, such as kerosene and diesel oil, further coal tar oils and oils of vegetable or aminal origin, and cyclic hydrocarbons, such as tetrahydronaphthalene and alkylated naphthalenes, are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, emulsifying or dispersing agent and possibly solvent.

Dusts may be prepared by mixing or grinding the active ingredients with a solid carrier, e.g., kieselguhr, talc, clay or fertilizers. Granules in various particle sizes may be prepared by applying the compositions to solid carriers.

Sprayable dispersions may be prepared with oils.

The active ingredients may be used in combination with fertilizers, other herbicides, fungicides and insecticides. The active ingredients a + b may be used in a ratio by weight of from 3:1 to 1:5.

The application rate of the compositions may vary, for instance from 0.5 to 3 kg per hectare.

The compositions are for example suitable for controlling Echinochloa crus-galli, Digitaria sanguinalis, Cyperaceen, Amaranthus spp., Alisma plantago-aquatica, Xanthium spp., Galium aparine, Lamium spp., Stellaria media, Matricaria spp., Poa spp., Lolium spp., and Alopecurus myosuroides without causing damage to crops such as Oryza sativa, Zea mays, Glycine hispida, Hordeum vulgare, Triticum aestivum and Linum usitatissimum.

The efficacy of the compositions according to the invention is illustrated in the following examples.

EXAMPLE 1

The following individual active ingredients and compositions thereof were sprayed, in an oil vehicle, onto the plants Oryza sativa, Zea mays, Echinochloa crus-galli, Setaria viridis, Cyperus esculentus, Alisma plantago-aquatica and Xanthium spp. at a growth height of from 1.5 to 18 cm in the form of a dispersion or emulsion in 500 liters of water per hectare.

I+IV:
3-isopropyl-2,1,3-benzothiadiazinone-(4)-2,2-dioxide + non-phytotoxic paraffin oil,
0.5 + 4.0 kg/ha, 1.0 + 4.0 kg/ha, 2.0+4.0 kg/ha, 4.0 + 4.0 kg/ha;

II+IV:
methyl N-3,4-dichlorophenylcarbamate + non-phytotoxic paraffin oil,
2.0+4.0 kg/ha and 4.0+4.0 kg/ha;

III+IV:
methyl N-3-chloro-4-bromophenylcarbamate + non-phytotoxic paraffin oil,
2.0+4.0 kg/ha and 2.5+4.0 kg/ha;

IV: non-phytotoxic paraffin oil, 4.0 kg/ha;

I+II+IV:
2.0 + 2.0 + 4.0 kg/ha;

I+III +IV:
1.0+2.0+4.0 kg/ha and 0.5+2.5+4.0 kg/ha.

After 10 to 14 days it was ascertained that the active ingredient compositions had more favorable crop plant compatibility than the individual active ingredients, combined with a superior action on the broadleaved and grassy weeds.

The results of the experiment are given in the following table:

| kg/ha | I + IV | | | |
|---|---|---|---|---|
| | 0.5+4.0 | 1.0+4.0 | 2.0+4.0 | 4.0+4.0 |
| Oryza sativa | 0 | 0 | 0 | 0 |
| Zea mays | 0 | 0 | 0 | 0 |
| Echinochloa crus-galli | 10 | 15 | 20 | 35 |
| Setaria viridis | 5 | 10 | 15 | 30 |
| Cyperus esculentus | 30 | 45 | 85 | 100 |

-continued

| kg/ha | I + IV 0.5+4.0 | 1.0+4.0 | 2.0+4.0 | 4.0+4.0 |
|---|---|---|---|---|
| Alisma plantago-aquatica | 25 | 45 | 70 | 100 |
| Xanthium spp. | 20 | 35 | 70 | 100 |

| kg/ha | II + IV 2.0 | 4.0 |
|---|---|---|
| Oryza sativa | 0 | 20 |
| Zea mays | 0 | 15 |
| Echinochloa crus-galli | 45 | 85 |
| Setaria viridis | 40 | 80 |
| Cyperus esculentus | 10 | 20 |
| Alisma plantago-aquatica | 25 | 50 |
| Xanthium spp. | 25 | 55 |

| kg/ha | III + IV 2.0+4.0 | 2.5+4.0 | 4.0+4.0 | IV 4.0 |
|---|---|---|---|---|
| Oryza sativa | 0 | 5 | 15 | 0 |
| Zea mays | 0 | 0 | 10 | 0 |
| Echinochloa crus-galli | 50 | 60 | 90 | 0 |
| Setaria viridis | 45 | 55 | 85 | 0 |
| Cyperus esculentus | 10 | 15 | 25 | 0 |
| Alisma plantago-aquatica | 30 | 40 | 65 | 0 |
| Xanthium spp. | 20 | 30 | 45 | 0 |

| kg/ha | I + II + IV 2.0 + 2.0 + 4.0 | I + III + IV 1.0 + 2.0 + 4.0 |
|---|---|---|
| Oryza sativa | 0 | 0 |
| Zea mays | 0 | 0 |
| Echinochloa crus-galli | 95 | 90 |
| Setaria viridis | 80 | 80 |
| Cyperus esculentus | 100 | 90 |
| Alisma plantago-aquatica | 100 | 100 |
| Xanthium spp. | 100 | 90 |

| kg/ha | I + III + IV 0.5 + 2.5 + 4.0 |
|---|---|
| Oryza sativa | 5 |
| Zea mays | 0 |
| Echinochloa crus-galli | 95 |
| Setaria viridis | 85 |
| Cyperus esculentus | 70 |
| Alisma plantago-aquatica | 95 |
| Xanthium spp. | 85 |

0 = no damage
100 = complete destruction

EXAMPLE 2

In the greenhouse, various plants were treated at a growth height of 4 to 25 cm with the following amounts of the following individual active ingredients and compositions thereof as emulsions, dispersions or aqueous solutions:

I 3-isopropyl-2,1,3-benzothiadiazinone-(4)-2,2-dioxide, 3 and 4 kg per hectare;

II 3-isopropyl-2,1,3-benzothiadiazinone-(4)-2,2-dioxide, sodium salt, 3 and 4 kg per hectare;

III 3-isopropyl-2,1,3-benzothiadiazinone-(4)-2,2-dioxide, dimethylamine salt, 3 and 4 kg per hectare;

IV 3-isopropyl-2,1,3-benzothiadiazinone-(4)-2,2-dioxide, diethanolamine salt, 3 and 4 kg per hectare;

VI methyl N-3,4-dichlorophenylcarbamate, 1 and 4 kg per hectare;
I+VI: 3+1 kg per hectare;
II+VI: 3+1 kg per hectare;
III+VI: 3+1 kg per hectare;
IV+VI: 3+1 kg per hectare.

After 12 to 18 days it was ascertained that the compositions had a better herbicidal action than their individual components, combined with the same good crop plant compatibility.

The results are given below:

| Active ingredient kg/ha | I 3 | 4 | II 3 | 4 | III 3 | 4 | IV 3 | 4 | VI 1 | 4 | I+VI 3+1 | II+VI 3+1 | III+VI 3+1 | IV+VI 3+1 |
|---|---|---|---|---|---|---|---|---|---|---|---|---|---|---|
| Crop plant: | | | | | | | | | | | | | | |
| Oryza sativa | 0 | 0 | 0 | 0 | 0 | 0 | 0 | 0 | 0 | 0 | 0 | 0 | 0 | 0 |
| Unwanted plants: | | | | | | | | | | | | | | |
| Echinochloa crus-galli | 25 | 35 | 30 | 40 | 25 | 40 | 20 | 30 | 25 | 85 | 90 | 97 | 92 | 90 |
| Cyperus esculentus | 75 | 97 | 78 | 97 | 75 | 96 | 74 | 95 | 5 | 20 | 100 | 100 | 100 | 100 |
| Eleocharis spp. | 70 | 90 | 72 | 95 | 70 | 90 | 67 | 87 | 10 | 55 | 100 | 100 | 100 | 100 |

0 = no damage
100 = complete destruction

The invention is hereby claimed as follows:

1. A herbicide composition comprising, as the herbicidal components, a herbicidally effective amount of a mixture of
   a. a compound of the formula

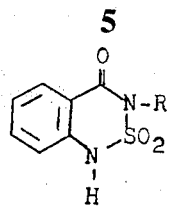

wherein R denotes lower alkyl or an alkali metal, alkaline earth metal, ammonium, lower hydroxyalkylamine or lower alkylamine salt of said compound, and b. a compound of the formula

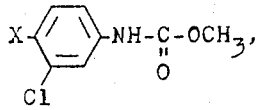

wherein X denotes chlorine or bromine, the weight ratio of (a) to (b) being in the range of 3:1 to 1:2.

2. A herbicide composition as claimed in claim 1 wherein R is isopropyl.

3. A process for suppressing growth of unwanted plants amidst crop plants which comprises applying to said unwanted plants a herbicidally effective amount of a herbicide composition as claimed in claim 1.

4. A process for suppressing growth of unwanted plants amidst crop plants which comprises applying to said unwanted plants a herbicidally effective amount of a herbicide composition as claimed in claim 2.

* * * * *